United States Patent [19]

Moberg

[11] 4,275,073

[45] Jun. 23, 1981

[54] FUNGICIDAL COMPOUNDS

[75] Inventor: William K. Moberg, Wilmington, Del.

[73] Assignee: E. I. Du Pont de Nemours and Company, Wilmington, Del.

[21] Appl. No.: 144,859

[22] Filed: Apr. 29, 1980

[51] Int. Cl.$^3$ .................. A01N 43/56; C07D 495/04; C07D 487/00

[52] U.S. Cl. ................................ 424/273 P; 548/370; 548/374; 548/375; 548/376; 548/377; 548/363; 548/358

[58] Field of Search ..................... 548/370; 424/273 P

[56] References Cited

U.S. PATENT DOCUMENTS 4,094,985 6/1978 Vladuchick .......................... 424/270

FOREIGN PATENT DOCUMENTS 54-44667 4/1979 Japan .

OTHER PUBLICATIONS

Perregaard et al, Bull. Soc. Chim. Belges 1977, vol. 86, p. 679.

*Primary Examiner*—Henry R. Jiles
*Assistant Examiner*—Natalia Harkaway

[57] ABSTRACT

Pentathiepinopyrazoles and pyrazolotrithiocarbonates, such as 7-methyl-7H-1,2,3,4,5-pentathiepino[6,7-c]pyrazole, useful for the control of fungi.

30 Claims, No Drawings

FUNGICIDAL COMPOUNDS

BACKGROUND OF THE INVENTION

This invention relates to fungicidal compounds.

Vladuchick, U.S. Pat. No. 4,094,985, discloses fungicidal isothiazoles of the formula

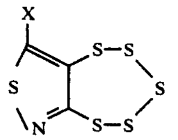

where X represents various defined substituents.

Perregaard, et al., *Bull. Soc. Chim. Belges,* 86, 679 (1977) discloses

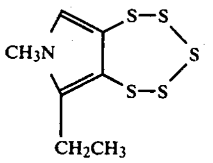

and other products.

No utility for the compound is found in the publication.

SUMMARY OF THE INVENTION

This invention relates to compounds of Formula I, to agricultural compositions containing them, to methods of use of these compounds as plant disease control agents, particularly foliar fungicides, and to processes for preparing them.

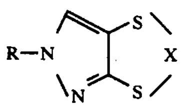

wherein

X is —S—S—S— or

and

R is H, $C_1$-$C_6$ alkyl, $C_5$-$C_6$ cycloalkyl,

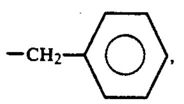

or 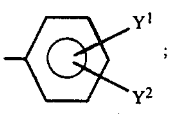

$Y^1$ and $Y^2$ independently are H, F, Cl, Br, p-methoxy, or p-nitro.

Intermediates for Preparation of Formula I Compounds

Intermediates of Formula II are disclosed.

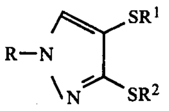

II wherein $R^1$ and $R^2$ are independently $C_1$-$C_4$ alkyl or benzyl; or $R^1$ and $R^2$ are identically $Si(R^3)_3$ or $Sn(R^3)_3$;

$R^3$ is $C_1$-$C_4$ alkyl or phenyl; and

R is as defined above except R may be H only where $R^1$ and $R^2$ are $Si(R^3)_3$ or $Sn(R^3)_3$.

Further, the intermediates of Formulae III, IV, and V are disclosed.

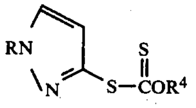

III

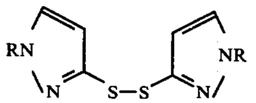

IV

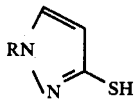

V wherein $R^4$ is $C_1$-$C_4$ alkyl; and

R is as defined for Formula I.

Illustrative Compounds

Preferred for reasons of high fungicidal activity are those compounds of Formula I wherein X is —S—S—S— or X is >C=S and R is H, $C_1$-$C_6$ alkyl. $C_5$-$C_6$ cycloalkyl or phenyl.

More preferred for reasons of higher fungicidal activity are those compounds of the preferred group wherein X is —S—S—S— and R is H, $C_1$-$C_6$ alkyl, $C_5$-$C_6$ cycloalkyl or phenyl.

Specifically preferred for reasons of highest fungicidal activity are the following compounds.

7-methyl-7H-1,2,3,4,5-pentathiepino[6,7-c]pyrazole, 7-phenyl-7H-1,2,3,4,5-pentathiepino[6,7-c]pyrazole, 7-cyclohexyl-7H-1,2,3,4,5-pentathiepino[6,7-c]-pyrazole.

7H-1,2,3,4,5-pentathiepino[6,7-c]pyrazole.

Examples of the intermediate compounds of Formula II are those of Formula II(a) where

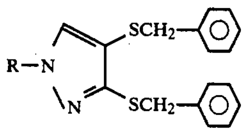

II(a)

where R is phenyl, methyl, and cyclohexyl.

Examples of the intermediate compounds of Formula III are those for which $R^4$ is ethyl and R' is H or methyl.

Examples of the intermediate compounds of Formulae IV and V are those where R is H or methyl.

Preparation

The compounds of this invention are obtained using a novel dithiol synthesis, the key step of which is a cycloaddition between a dithioacetylene and a diene or 1,3-dipole to give an aromatic or heteroaromatic 1,2-dithioether. The dithiol may then be obtained by cleavage of the dithioether, using standard methods that will vary according to the groups attached to sulfur.

Illustratively, a sydnone and a dithioacetylene are reacted to form a pyrazole dithioether:

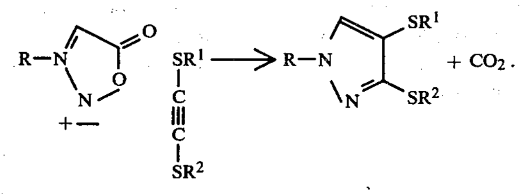

where $R = C_1$–$C_6$ alkyl, $C_5$–$C_6$ cycloalkyl, benzyl, phenyl or substituted phenyl as previously defined;

$R^1$ and $R^2 = C_1$–$C_4$ alkyl or benzyl.

For the pentathiepins of this invention (Formula I, where X is —S—S—S—), another novel synthesis has been discovered, namely the reaction of 3-mercaptopyrazoles or their salts with sulfur halides:

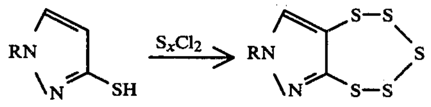

where

R=H, $C_1$–$C_6$ alkyl, $C_5$–$C_6$ cycloalkyl, benzyl, phenyl, or substituted phenyl as previously defined; and

X=1–4.

The reactions used to prepare the compounds of this invention are further described as follows:

A. Cycloaddition (reaction of sydnone and acetylene)

R may be alkyl, aryl, heteroaromatic, or substituted amino. Very many sydnones are known; see, for example, F. H. C. Stewart, *Chem. Rev.*, 64, 129 (1964); W. D. Ollis and C. A. Ramsden, *Adv. Heterocyclic Chem.*, 19, 1 (1976). R may not be H in the sydnone, but products of Formula I, where R=H may be obtained from the compound where $R^1$=$R^2$=R=benzyl. All three benzyl groups may be removed simultaneously by dissolving metal reductions, using the conditions described in "B" but with the amount of reducing metal increased by 50%. The product where $R^1$=$R^2$=R=H may then be converted to the trithiocarbonate or pentathiepin as in sections C and D below. Subsequent reactions with alkylating or arylating reagents (alkyl halides, alkyl sulfonate esters, activated halobenzenes or nitrobenzenes) provide an alternative route to other compounds of Formula I.

$R^1$ and $R^2$ may be lower alkyl or benzyl. They may be different, but for the present invention it is preferred that they be the same, and particularly benzyl, since it is desirable to remove them simultaneously.

Various molar ratios of sydnone and acetylene are operable, and 100% excess or greater of either reagent can be used to maximize the yield based on the other reagent. It is preferred to use the sydnone in 10–50% excess, as it is usually the less stable component.

The reaction may be conducted in any solvent or mixture of solvents having the appropriate physical properties (i.e., boiling point in the case of reactions at ambient pressure). The reaction mixture need not be homogeneous provided efficient stirring is used. Mixtures of the neat reactants have been known to react suddenly, releasing a large volume of gas in a short time; this tendency is minimized by use of a solvent, which dilutes the reactants and which can remove heat by refluxing. Useful classes of solvents include aliphatic hydrocarbons (e.g. decalin, n-decane, mineral oil), aromatic hydrocarbons (e.g. xylene, cumene, tetralin), aromatic ethers (e.g. anisole, diphenyl ether), aromatic halides (e.g. di- and trichlorobenzenes), aromatic esters (e.g. dialkylphthalates, ethyl benzoate), nitrobenzene, aliphatic ethers (di- and triglyme), aliphatic sulfoxides and sulfones (e.g. dimethyl sulfoxide, sulfolane), aliphatic amides (e.g. dimethylformamide, dimethylacetamide), or polysiloxanes.

The reaction temperature will vary from 50°–300° C. depending upon the nature of R, $R^1$ and $R^2$. For reactions at atmospheric pressure, the temperature is adjusted to give a steady evolution of gas, and it is usually increased gradually as the reactants are consumed. For many substrates, a range of 140°–200° C. is optimal.

The pressure may be 0.1–100 atm. Atmospheric pressure is preferred because the extent of reaction is easily monitored by the volume of gas produced.

Reaction time will vary with substrates, temperature, pressure, and scale. Reactions using excess sydnone are run until gas evolution becomes slow, during which time 110–150% of the theoretically expected volume of gas is collected.

When the product is lower boiling than the solvent, simple distillation may afford pure product. In general, however, the solvent is removed by distillation, preferably at reduced pressure. The crude residue may be useful as is, or the product may be further purified by standard techniques including distillation, extraction into aqueous acid, precipitation of salts or complexes, crystallization, chromatography, and the like.

B. Removal of $R^1$ and $R^2$

The method of choice will depend somewhat on the nature of R, $R^1$ and $R^2$. In all cases, however, it is important to exclude air from the reaction to avoid oxidized by-products.

When $R^1$ and $R^2$ are alkyl or arylalkyl groups, hydrolytic or reductive cleavage is possible. Hydrolytic conditions are especially suited to $R^1$=$R^2$=benzyl, or tert-alkyl; they include heating with concentrated aqueous mineral acid, hydrogen bromide in acetic acid, iodotrimethylsilane in acetonitrile or chloroform, and the like.

Reductive cleavage is more generally applicable and includes such methods as dissolving metals in amine or alcohol solvents, with or without cosolvents; lithium naphthalenide in tetrahydrofuran and the like; or electrochemical reduction in acetonitrile, dimethylformamide, and the like, using suitable salts as electrolyte. Preferred for reasons of cost and ease of workup in reduction by dissolving metal, particularly sodium, in an amine solvent, particularly ammonia. Addition of a cosolvent such as tetrahydrofuran, dimethoxyethane, and the like is desirable to make the substrate more soluble. Suitable concentrations of substrate in 1:1 mixtures of ammonia and cosolvent are 0.05–0.50 molar. The amount of sodium required is 3.0–4.5 equivalents, and a moderate excess does not seem deleterious; about 4.0 g-atoms of sodium per mole of substrate is preferred. Reduction is conducted at −100° to −30° C., preferably at −40° to −30° C. Sodium is added in small pieces at 0.05–1.0 g. atom per hour, depending on scale. A slurry usually develops, and good agitation is important to ensure complete reduction. Stirring is continued for 0.5–2 hours, excess amine hydrochloride, preferably pyridinium or ammonium chloride, is added to decompose unreacted sodium, and ammonia is allowed to evaporate. The dithiol may be isolated from the residue by standard techniques, but it is preferable to carry out the subsequent transformations in situ.

C. Trithiocarbonate Formation

Pyrazole dithiols, either isolated as such or as part of a mixture resulting from removal of $R^1$ and $R^2$ as described above, are converted to the trithiocarbonates of this invention by standard methods. Thiophosgene, in combination with acid acceptors such as triethylamine, pyridine, alkali metal hydroxides and carbonates, and the like, may be used in a variety of solvents such as water, aliphatic alcohols, aliphatic ethers, aromatic hydrocarbons, chlorinated hydrocarbons, and the like, at temperatures of −20° to 50° C. Improved yields result from reagents in which the chlorines of thiophosgene have been replaced with nitrogen-containing heterocycles, in particular 1,1′-thiocarbonyldiimidazole. Hydroxylic solvents decompose these reagents, but most other solvents may be used including aliphatic ethers, aliphatic esters, chlorinated hydrocarbons, aromatic hydrocarbons, and the like. The reagent is added to the dithiol mixture as a solid, or better as a solution in a solvent such as dichloromethane. One to two equivalents are used, preferably 1.5 to 2.0 equivalents in small-scale reactions. The reaction mixture is held at −20° to 50° C., preferably at room temperature. Whereas the reaction takes place rather quickly and the products are stable in the reaction medium, the length of reaction at room temperature is a matter of convenience. To assure a rapid reaction, the addition of 0.1 equivalent or more of a tertiary amine such as triethylamine is recommended.

The product is recovered by standard techniques. Water-miscible solvents, if any, are removed by evaporation, and the residue is partitioned between aqueous acid of pH 0.5 or higher, and an immiscible solvent such as dichloromethane. Removal of organic solvent leaves a residue that can be purified by standard techniques including crystallization, distillation, chromatography, and the like.

D. Pentathiepin Formation from Dithiols

Pyrazole dithiols, either isolated as such or as part of a mixture resulting from removal of $R^1$ and $R^2$ as described above, may be converted to the pentathiepins of this invention by reaction with sulfur monochloride ($S_2Cl_2$) according to U.S. Pat. No. 4,094,985. Sulfur dichloride ($SCl_2$) or bis(toluenesulfonyl) trisulfane may be substituted for $S_2Cl_2$. Yields are not generally as good for pyrazoles as for the isothiazoles of U.S. Pat. No. 4,094,985, however; and thus, two new methods have been devised.

In the first method, the chlorines of sulfur monochloride are replaced with nitrogen-containing heterocycles by known procedures to give N,N′-dithiobissuccinimide, N,N′-dithiobisbenzimidazole, and the like (D. N. Harpp, K. Steliou, and T. H. Chan, *J. Amer. Chem. Soc.*, 100, 1222 (1978) and references therein). The benzimidazole reagent represents a good balance between reactivity and shelf stability and is thus preferred. These reagents are proposed in the literature to be stable toward disproportionation, unlike $S_2Cl_2$, but they nevertheless give the unexpected result of selectivity transferring three sulfurs to form pentathiepins. For convenience, it is generally preferred to add the disulfide reagent, as a solid or better as a solution, to a solution or slurry of the pyrazole dithiol. The temperature is maintained at −80° to 50° C., preferably at 0° to 30° C., and the addition rate is 0.01 to 1.0 mol of reagent per hour, depending upon scale. The mixture is then allowed to stir at −80° to 100° C., preferably at room temperature, for 0.5 to 24 hours. Reaction periods longer than 1 hour are not generally required, but neither are they deleterious to yield. The use of hydroxylic solvents is limited by the instability of certain disulfide reagents. Most other solvents can be used, including aliphatic ethers, aliphatic esters, chlorinated hydrocarbons, aromatic hydrocarbons, and the like.

In the second new method, pretreatment of the pyrazole dithiols with organosilicon or organotin halides to form derivative A (M=Si or Sn, $R^3$=$C_1$-$C_4$ alkyl or phenyl) allows

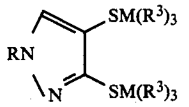

A pentathiepin formation in good to excellent yield using $S_2Cl_2$. $SCl_2$, $S_3Cl_2$, or bis(toluenesulfonyl)-trisulfane may also be used, but $S_2Cl_2$ is preferred on the basis of cost and yield. The pyrazole dithiol is slurried or dissolved in a non-hydroxylic solvent such as an aliphatic ether, an aliphatic ester, an aromatic hydrocarbon, a chlorinated hydrocarbon, or a mixture of these, mixtures such as dimethoxyethane-dichloromethane are preferred because they give reaction mixtures that are easily stirred. Being careful to maintain a nitrogen atmosphere in the reaction vessel, an acid acceptor such as a tertiary amine or an alkali metal carbonate or bicarbonate is added. The mixture is then agitated at −80° to 100° C., preferably at 5°–30° C., while the organometallic halide is added neat or as a solution in one of the solvents listed above. The rate of addition depends upon the halide, the maximum temperature desired, and the efficiency of cooling. For each halide, the cooling and addition rate are balanced so as to hold the temperature within the preferred range. The organometallic halides that may be used include trialkylhalosilanes such as chlorotrimethylsilane, triphenylchlorosilane, trialkyltin halides such as trimethyl or tributyltin chloride, triphenyltin chloride, and the like. Chlorotrimethylsilane is preferred because of cost and volatility; and 2.0–6.0 mols are used per mole of dithiol; the preferred range is 3.0–4.0 mols. The amount of acid acceptor is 1.0–1.5 mole per mole of organometallic halide.

The reaction is allowed to continue at −80° to 100° C., preferably 20°–40° C. The time required varies widely according to the organometallic halide; for chlorotrimethylsilane, 1–2 hours is usually sufficient but periods up to 24 hours are not harmful. The mixture is then maintained at −80° to 100° C., preferably 5°–30° C., while $S_2Cl_2$ is added neat or as a solution in one of the solvents listed above. As before, the addition rate and cooling are balanced to maintain the desired temperature range. The amount of $S_2Cl_2$ is 1.5–4.0 mole per mole of dithiol, preferably 2.2–2.5 mole. After addition, the mixture is held at −80° to 100° C., preferably at room temperature, until pentathiepin formation is complete. This requires typically 1–2 hours for bis(trimethylsilyl)dithiols, but periods as long as 72 hours have been used with no decrease in yield.

For both new methods, the pentathiepin is isolated and purified using procedures essentially identical to those described above for trithiocarbonates.

The choice of pentathiepin-forming methods will vary somewhat according to the dithiol. In general, the second method (organometallic halide followed by $S_2Cl_2$) is preferable, all reagents being commercially available.

E. Pentathiepin Formation from Monothiols

An alternative to the pentathiepin synthesis of section D has been found in the reaction of 3-mercaptopyrazoles (V) with sulfur halides, whereby a new C-S bond and the polysulfide ring are formed in one operation. This method is operable for all the R groups listed under Formula I, and it is preferred for R=H.

Any of the sulfur halides $S_xCl_2$, X=1–4, may be used. $S_2Cl_2$ is preferred since it is commercially available and readily purified. Mercaptan —$S_2Cl_2$ molar ratios between 1:2.5 and 1:3.0 are preferable. A base is not required, but in some cases, an ammonium or alkali metal salt of the mercaptan may give cleaner products than the mercaptan itself. The reaction may be run in any solvent in which sulfur halides are stable; polar solvents, and especially dimethylformamide—chlorinated hydrocarbon mixtures, have been found to give the cleanest products. Less polar solvents give comparable results if a Lewis acid is added, a typical combination being chloroform containing 1.5 mols of titanium tetrachloride per mol of mercaptan.

Reactions are allowed to proceed at 0°–100° C., preferably at room temperature, until complete; solvent and excess sulfur halide are removed by distillation at reduced pressure; and the pentathiepin is recoverd from the residue using standard techniques. In favorable cases, the product may precipitate as formed or may be forced out of solution by adding another solvent, so that solvents and sulfur halide may be removed by simple filtration.

The 3-mercaptopyrazoles required for this synthesis may be prepared from 3-aminopyrazoles by diazotization, xanthate coupling, and hydrolysis:

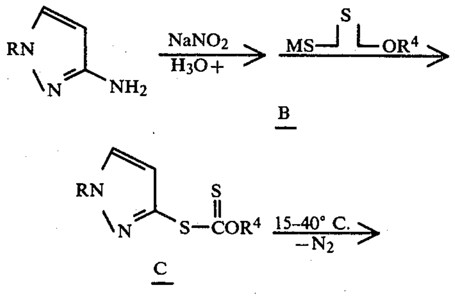

B

C

-continued

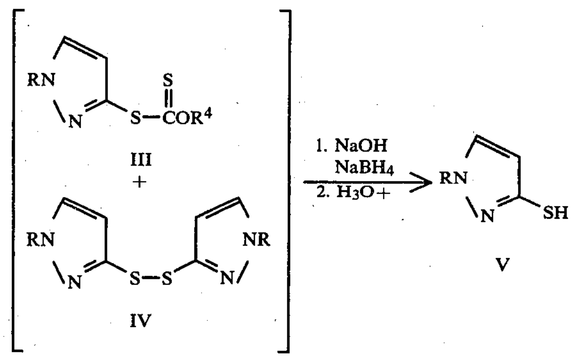

III

IV

V

Diazotization is conducted in water at −5° to +10° C. using one equivalent of sodium nitrite and two equivalents of mineral acid, preferably HCl. Addition of an xanthic acid salt B (M is an alkali metal, preferably potassium; and $R^4$ is $C'_1$–$C_4$ alkyl, preferably ethyl) at the same temperature gives the azo intermediate C, which loses nitrogen on warming to give predominantly III. A slight excess of B, preferably 1.1 to 1.2 equivalents, is used. The cleanest product is obtained if an organic solvent is present while B is added, so that C is extracted into the organic phase as it forms. The organic solution is then removed from the reaction vessel while still cold, so that decomposition of C may proceed in the absence of water. Almost any water-immiscible solvent is operable; dichloromethane is especially useful because it retains little water, and its low boiling point helps to moderate the exothermic reaction. A large vessel is recommended to allow for vigorous foaming, and cooling may be advisable in large scale runs. When the spontaneous reaction subsides, the solution is warmed until gas evolution stops and evaporated. Although the crude xanthate may be purified by standard means, it is usually preferable to hydrolyze the crude product directly to the mercaptan using aqueous sodium or potassium hydroxide.

The xanthate is almost always accompanied by some disulfide of Formula IV. This may be reduced to the desired mercaptan simultaneously with xanthate hydrolysis by adding sodium borohydride to the reaction mixture.

When hydrolysis and reduction are complete, the basic solution is washed with an organic solvent to remove inert impurities and then acidified with mineral acid to precipitate the mercaptan V, which is removed by extraction with organic solvent. The extract may be concentrated, but it is preferable to use the solution directly for pentathiepin formation since the neat mercaptan is susceptible to air oxidation back to disulfide IV. Any water immiscible solvent in which V is soluble may be used, chlorinated hydrocarbons being especially convenient.

In the following examples, all parts are by weight and temperatures are in degrees Centigrade unless otherwise specified; nmr chemical shifts are "δ", ir frequencies are $\gamma_{max}$ and mass spectrum values are m/e.

EXAMPLE 1

3,4-Bis(phenylmethylthio)-1-methyl-1H-pyrazole

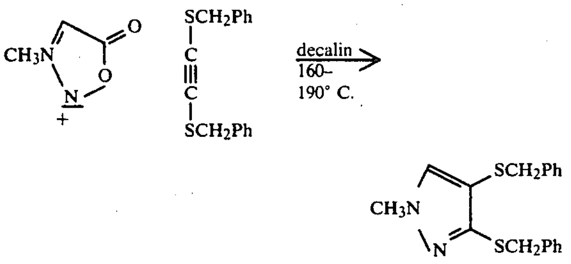

A mixture of N-methylsydnone[1] (216 g, 2.16 mol), bis(benzylthio)acetylene[2] (437 g, 1.62 mol), and decalin (490 ml) was stirred and warmed to 160°. The temperature was then increased gradually over 7 hours to 193°, during which time 70 l of gas was evolved. Decalin was distilled off at aspirator pressure, and the residual oil was chromatographed over silica gel (dichloromethane-methanol gradient) to give 193 g (36% based on the dithioacetylene) of 3,4-bis(phenylmethylthio)-1-methyl-1H-pyrazole as an oil: nmr ($CDCl_3$) 3.70 and 3.73 (total of 5H, two singlets), 4.24 (2H, singlet), 6.91 (1H, singlet), 7.0–7.4 (10H, multiplet).

[1] D. L. Hammick and D. J. Voaden, *J. Chem. Soc.*, 3303 (1961).
[2] E. Fromm, H. Benzinger, and F. Schaefer, *Liebigs Ann. Chem.*, 394, 325 (1912).

Samples prepared similarly showed: ir (neat) 3025, 2920, 1600, 1490, 1340, 1140, 1060, 785, 760, 700 $cm^{-1}$; mass spectrum 326.0893 ($C_{18}H_{18}N_2S_2$=326.0911); analysis for $C_{18}H_{18}N_2S_2$ (mw 326.47)

| | |
|---|---|
| Calc. C 66.25 | C Found C 68.32 |
| H 5.56 | H. 5.54 |
| N 8.58 | N 8.31 |
| S 19.61 | S 20.12 |

Other compounds available similarly:

3,4-Bis(phenylmethylthio)-1-ethyl-1H-pyrazole

Oil; nmr ($CDCl_3$) 1.30 (3H, triplet, J=7 Hz), 3.68 (2H, singlet), 3.90 (2H, quartet, J=7 Hz), 4.20 (2H, singlet) 6.81 (1H, singlet), 6.9–7.4 (10H, multiplet); ir(neat) 3020, 3000, 2950, 1500, 1450, 1340, 1140, 1065, 1045, 765, 695 $cm^{-1}$.

3,4-Bis(phenylmethylthio)-1-phenyl-1H-pyrazole

Oil; nmr ($CDCl_3$) 3.80 (2H, singlet), 4.38 (2H, singlet), 7.0–7.6 (11H, multiplet); ir (neat) 3080, 1605, 1515, 1330, 1060, 950, 760, 695 $cm^{-1}$.

3,4-Bis(phenylmethylthio)-1-cyclohexyl-1H-pyrazole

Oil; nmr ($CDCl_3$) 1.0–2.1 (10H, multiplet), 3.7–4.0 (3H, multiplet with singlet at 3.74), 4.28 (2H, singlet), 6.7–7.5 (11H, multiplet with singlet at 6.94); ir (neat) 3050, 2925, 2850, 1500, 1450, 1430, 765, 700 $cm^{-1}$.

EXAMPLE 2

2-Methyl-2H-[1,3]dithiolo[4,5-c]pyrazole-5-thione

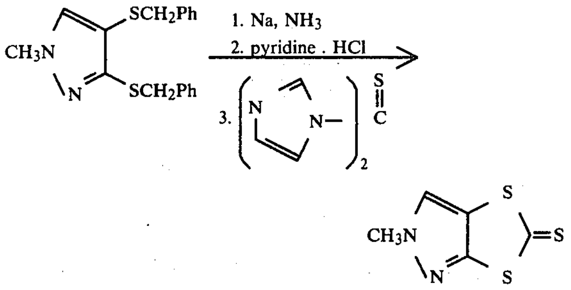

A solution of 3,4-bis(phenylmethylthio)-1-methyl-1H-pyrazole (6.52 g, 20 mmol) in 100 ml of ammonia and 100 ml of dimethoxyethane was stirred at reflux while sodium metal (1.84 g, 80 mg-atom) was added in small pieces over 1 hour. After another hour at reflux, pyridine hydrochloride (9.2 g, 80 mmol) was added, ammonia was allowed to evaporate under $N_2$ purge, and the residual slurry was stirred under $N_2$ while a solution of thiocarbonyldiimidazole (7.9 g of 90% reagent, 40 mmol) in 100 ml of dichloromethane was added dropwise over 30 min. The mixture was stirred another 30 minutes, allowed to stand overnight, and evaporated. The residue was taken up in dichloromethane, and the solution was washed with 2 N aqueous hydrochloric acid, water, and brine, dried over magnesium sulfate, and evaporated to give 5.1 g of brown solid. Trituration with ethyl acetate followed by crystallization from the same solvent gave 1.35 g of orange needles, mp 147°–149°. Chromatography of the mother liquors and crystallization from ethyl acetate gave another 0.36 g, mp 145°–148°, for a combined yield of 1.72 g (46%).

Samples prepared similarly showed: nmr ($CDCl_3$) 4.02 (3H, singlet), 7.42 (1H, singlet); ir (KBr) 1520, 1140, 1065, 1045, 1025, 875, 805 $cm^{-1}$; mass spectrum 187.9526 ($C_5H_4N_2S_3$=187.9536); analysis for $C_5H_4N_2S_3$ (mw 188.28):

| | |
|---|---|
| Calc. C 31.90 | Found C 32.20, 32.28 |
| H 2.14 | H 2.31, 2.32 |
| N 14.88 | N 15.00, 14.77 |
| S 51.08 | S 51.24, 51.12 |

Other compounds available similarly:

2-Ethyl-2H-[1,3]dithiolo[4,5-c]pyrazole-5-thione

M.p. 90°–92°; nmr ($CDCl_3$) 1.55 (3H, triplet, J=7 Hz), 4.29 (2H, quartet, J=7 Hz), 7.45 (1H, singlet); ir (nujol) 3100, 1140, 1060, 1045, 860, 820 $cm^{-1}$.

2-Phenyl-2H-[1,3]dithiolo[4,5-c]pyrazole-5-thione

M.p. 133°–134°; nmr ($CDCl_3$) 7.3–7.8 (5H, multiplet); 7.94 (1H, singlet); ir (nujol) 1600, 1500, 1340, 1200, 1075, 1055, 1040, 950, 865, 770, 750 $cm^{-1}$.

2-Cyclohexyl-2H-[1,3]dithiolo[4,5-c]pyrazole-5-thione

Mp 104°–105° C.; nmr ($CDCl_3$) 1.2–2.3 (10H, multiplet), 3.9–4.3 (1H, multiplet), 7.45 (1H, singlet); ir (nujol) 3100, 1500, 1135, 1065, 1050, 865, 800 $cm^{-1}$.

EXAMPLE 3

7-Methyl-7H-1,2,3,4,5-pentathiepino[6,7-c]pyrazole

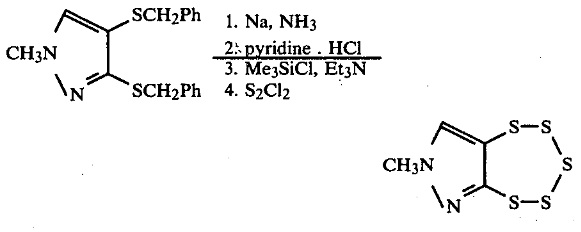

3,4-Bis(phenylmethylthio)-1-methyl-1H-pyrazole (3.26 g, 10 mmol) was reduced with sodium in ammonia-dimethoxyethane as in Example 2. The slurry remaining after removal of ammonia was maintained under $N_2$ and chilled in ice while imidazole (0.1 g) and triethylamine (5.5 g, 50 mmol) were added in one portion, followed by a solution of chlorotrimethylsilane (4.35 g, 40 mmol) in 50 ml of dichloromethane added dropwise over 30 minutes. The resulting slurry was stirred at room temperature for 1 hour, at 40° for another hour, and then again at room temperature while a solution of $S_2Cl_2$ (3.38 g 25 mmol) in 100 ml of dichloromethane was added over 1 hour. The mixture was allowed to stand under $N_2$ for 72 hours, and then water was added, followed by enough 2 N aqueous sodium hydroxide to bring the pH to ca. 3. The organic phase was washed with water and brine, dried over magnesium sulfate, and evaporated to leave 3.9 g of residue. Chromatography over silica gel (dichloromethane-petroleum ether gradient) followed by crystallization from ethyl acetate-hexanes gave 0.37 g, m.p. 114°-116°, and 0.14 g, m.p. 110°-112°, for a total of 0.51 g (21%) of 7-methyl-7H-1,2,3,4,5-pentathiepino-[6,7-c]pyrazole Samples prepared similarly showed: nmr ($CDCl_3$) 3.87 (3H, singlet), 7.62 (1H, singlet); ir (KBr) 3120, 1480, 1350, 1135, 1000, 850, 715, 685 $cm^{-1}$; mass spectrum 239.8980 ($C_4H_4N_2S_5$=239.8978), 175.9534 ($C_4H_4N_2S_3$=175.9536); analysis for $C_4H_4N_2S_5$ (mw 240.39):

| | |
|---|---|
| Calc. C 19.99 | Found C 20.27 |
| H 1.68 | H 1.91 |
| N 11.65 | N 11.59 |
| S 66.68 | S 66.66 |

Other compounds available similarly:

7-Ethyl-7H-1,2,3,4,5-pentathiepino[6,7-c]pyrazole

M.p. 54°-56°; nmr ($CDCl_3$) 1.50 (3H, triplet, J=7 Hz), 4.16 (2H, quartet, J=7 Hz), 7.66 (1H, singlet); ir (neat) 3180, 3100, 1490, 1440, 1340, 1135, 820, 700, 690 $cm^{-1}$; mass spectrum 253.9120 ($C_5H_6N_2S_5$=253.9134), 189.9686 ($C_5H_6N_2S_3$=189.9695).

7-Phenyl-7H-1,2,3,4,5-pentathiepino[6,7-c]pyrazole

M.p. 113°-115°; nmr ($CDCl_3$) 7.2-7.8 (5H, multiplet), 8.10 (1H, singlet); ir (nujol) 1605, 1505, 1190, 1050, 965, 825, 760, 770 $cm^{-1}$; mass spectrum 301.9111 ($C_9H_6N_2S_5$=301.9134), 237.9669 ($C_9H_6N_2S_3$=237.9692). The structure of this compound was confirmed by X-ray crystallographic analysis.

7-Cyclohexyl-7H-1,2,3,4,5-pentathiepino[6,7-c]pyrazole

Mp 73°-75° C.; nmr ($CDCl_3$) 1.2-2.3 (10H, multiplet), 3.8-4.2 (1H, multiplet), 7.60 (1H, singlet); ir (nujol) 3100, 1150, 1135, 985, 895, 760 cm; mass spectrum 307.9600 ($C_9H_{12}N_2S_5$=307.9603), 244.0159 ($C_9H_{12}N_2S_3$=244.0162).

EXAMPLE 4

Carbonodithioic Acid O-Ethyl-S-(1-methyl-1H-pyrazol-3-yl) Ester and 3,3'-Dithiobis(1-methyl-1H-pyrazole)

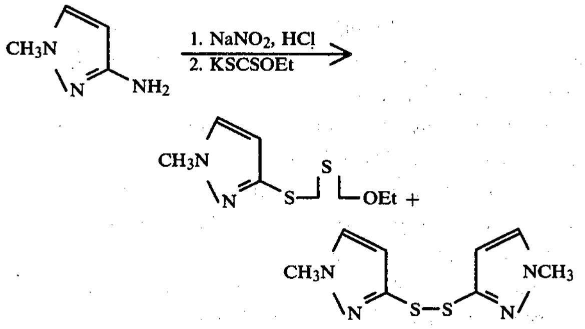

A solution of 3-amino-1-methylpyrazole (9.7 g, 0.10 mol; prepared according to G. Ege and P. Arnold, *Synthesis,* 52 (1976)) in a mixture of 17 ml (0.20 mol) of concentrated HCl and 85 ml of water was stirred at 10° while solid sodium nitrite (0.10 mol, 6.9 g) was added over 30 minutes. The solution was stirred at 10° for 15 minutes, 75 ml of dichloromethane was added, and the two-phase mixture was stirred at 10°-12° while solid potassium ethylxanthate was added in portions over 20 minutes. After another 15 minutes of stirring at 10°, the organic layer was separated, the aqueous layer was washed with 25 ml of dichloromethane, and the combined organic phases were washed with brine. Gas evolution began as the solution warmed, and when it subsided, the solution was refluxed until no more gas was evolved. Evaporation left 17.9 g of an organic oil containing at least 10 g (50%) of carbonodithioic acid O-ethyl-S-(1-methyl-1H-pyrazol-3-yl)ester. Pure samples of this compound, obtained by chromatography, showed:

$n^{25}_D$ 1.5898; ir (neat) 3175, 1500, 1240, 1045, 970, 760, 695 $cm^{-1}$; nmr ($DCDl_3$) 1.35 (3H, triplet, J=7), 4.00 (3H, singlet), 4.65 (2H, quartet, J=7), 6.52 (1H, doublet, J=2), 7.51 (1H, doublet, J=2).

The crude product also contained at least 2 g (18%) of 3,3'-dithiobis(1-methyl-1H-pyrazole).

Pure samples of this compound showed: m.p. 82°-87° C.; ir (nujol) 3125, 1500, 1285, 1170, 765 $cm^{-1}$; nmr ($CDCl_3$) 3.92 (3H, singlet), 6.52 (1H, doublet, J=2), 7.39 (1H, doublet, J=2).

Other compounds available similarly:

Carbonodithioic Acid O-Ethyl-S-(1H-pyrazol-3-yl) Ester $n^{24}_D$ 1.6150; ir (neat) 3200, 1240, 1110, 1040, 770 $cm^{-1}$; nmr ($CDCl_3$) 1.32 (3H, triplet, J=7), 4.65 (2H, quartet, J=7), 6.65 (1H, doublet, J=3), 7.83 (1H, doublet, J=3), 12.3 (1H, broad).

EXAMPLE 5

7-Methyl-7H-1,2,3,4,5-pentathiepino[6,7-c]pyrazole

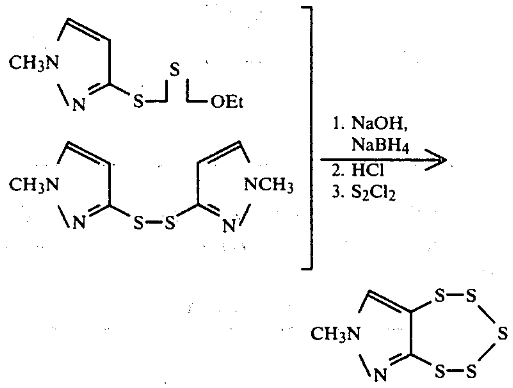

A xanthate-disulfide mixture (104 g; prepared from 0.6 mol of 3-amino-1-methylpyrazole by the procedure of Example 4) was stirred with a solution of sodium hydroxide (1.2 mol, 48 g) and 240 ml of water, $NaBH_4$ (0.06 mol, 2.3 g) was added in portions, and the mixture was warmed under $N_2$ to 80°-85° for 1.5 hours.

The mixture was cooled, washed with 100 ml of carbon tetrachloride, and brought to pH 2 by dropwise addition of 105 ml of concentrated HCl. The oil that separated was washed into a total of 180 ml of carbon tetrachloride, and the extract was dried over $Na_2SO_4$ and separated into six equal parts. One part was evaporated to give 6.7 g of 3-mercapto-1-methylpyrazole (59% from 1-amino-3-methylpyrazole) as an oil; nmr ($CCl_4$) 3.5 (1H, broad), 3.84 (3H, singlet), 6.18 (1H, doublet, J=2), 7.30 (1H, doublet, J=2).

Another 30-ml portion of the carbon tetrachloride extract was added dropwise over 10 minutes to a solution of $S_2Cl_2$ (0.18 mol, 23.9 g, 14.2 ml) and 30 ml of dimethylformamide. After coming spontaneously to 60°, the solution returned to room temperature and was stirred for 48 hours under $N_2$. Concentration under reduced pressure left a sticky solid that was washed with water and dried to 12.3 g. This was suspended in 100 ml of hot ethyl acetate and filtered, and the filtrate was evaporated to 9.1 g which was crystallized from carbon tetrachloride to give 7-methyl-7H-1,2,3,4,5-pentathiepino[6,7-c]-pyrazole, m.p. 94°-102°, having the same nmr spectrum as the product of Example 3.

Compounds available similarly:
7H-1,2,3,4,5-pentathiepino[6,7-c]pyrazole

M.p. 129°-133°; nmr ($CD_3SOCD_3$) 8.37 (1H, singlet), 9.5 (1H, broad); ir (nujol) 3100, 1280, 1235, 820 $cm^{-1}$; mass spectrum 225.8826 ($C_3H_2N_2S_5$=225.8821), 161.9374 ($C_3H_2N_2S_3$=161.9380).

Illustrative compounds which can be prepared using the general procedures of Example 1 are shown in Table 1. These compounds are usually liquids.

TABLE 1

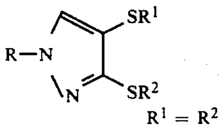

| R | $R^1 = R^2$ |
|---|---|
| $-CH_3$ | $-CH_2C_6H_5$ |

TABLE 1-continued

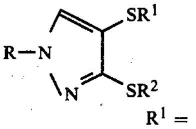

| R | $R^1 = R^2$ |
|---|---|
| $-CH_3$ | $-CH_3$ |
| $-CH_3$ | $-Si(CH_3)_3$ |
| $-CH_3$ | $-Sn(n-C_4H_9)_3$ |
| $-C_2H_5$ | $-CH_2C_6H_5$ |
| $-C_2H_5$ | $-Si(CH_3)_3$ |
| $-CH_2CH_2CH_3$ | $-CH_2C_6H_5$ |
| $-CH(CH_3)_2$ | $-CH_2C_6H_5$ |
| $-CH(CH_3)_2$ | $-Sn(n-C_4H_9)_3$ |
| $-CH_2CH_2CH_2CH_3$ | $-CH_2C_6H_5$ |
| $CH_2$<br>$-CCH_2CH_2CH_3$ | $-CH_2C_6H_5$ |
| $-CH_2CH(CH_3)_2$ | $-CH_2C_6H_5$ |
| $-C(CH_3)_3$ | $-CH_2C_6H_5$ |
| $-C(CH_3)_3$ | $-Si(CH_3)_3$ |
| 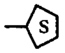 | $-CH_2C_6H_5$ |
| 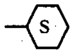 | $-CH_2C_6H_5$ |
| 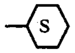 | $-Si(CH_3)_3$ |
| 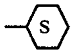 | $-CH(CH_3)_2$ |
| $-C_6H_5$ | $-CH_2C_6H_5$ |
| $-C_6H_5$ | $-C_2H_5$ |
| $-C_6H_5$ | $-CH(CH_3)_2$ |
| $-C_6H_5$ | $-Si(CH_3)_3$ |
| $-C_6H_5$ | $-Sn(n-C_4H_9)_3$ |
| $-CH_2C_6H_5$ | $-CH_2C_6H_5$ |
| $-CH_2C_6H_5$ | $-C(CH_3)_3$ |
| 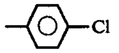 | $-CH_2C_6H_5$ |
| 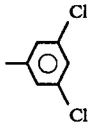 | $-CH_2C_6H_5$ |
| 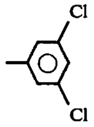 | $-Si(CH_3)_3$ |
| 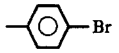 | $-CH_2C_6H_5$ |
| 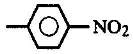 | $-CH_2C_6H_5$ |
| 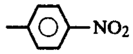 | $-C(CH_3)_3$ |
| 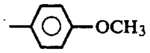 | $-CH_2C_6H_5$ |
| 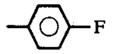 | $-CH_2C_6H_5$ |
| 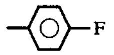 | $-Si(CH_3)_3$ |
| 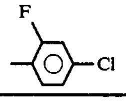 | $-CH_2C_6H_5$ |

Illustrative compounds which can be prepared using the general procedure of Example 2 are shown in Table 2.

TABLE 2

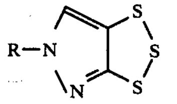

| R | mp° C. |
|---|---|
| H | |
| $-CH_3$ | 147–149 |
| $-C_2H_5$ | 90–92 |
| $-CH_2CH_2CH_3$ | |
| $-CH(CH_3)_2$ | |
| $-CH_2CH_2CH_2CH_3$ | |
| $CH_3$<br>\|<br>$-CHCH_2CH_2CH_3$ | |
| $-CH_2CH(CH_3)_2$ | |
| $-C(CH_3)_3$ | |
| 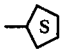 | |
| 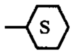 | 104–105 |
| 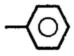 | 133–134 |
| 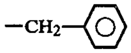 | |
| 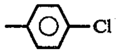 | |
| 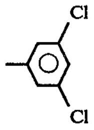 | |
| 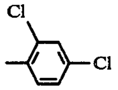 | |
| 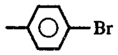 | |
| 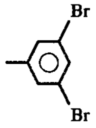 | |
| 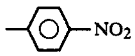 | |
| 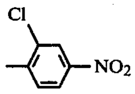 | |
| 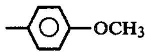 | |
| 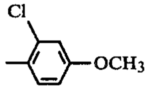 | |
| 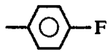 | |
| 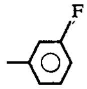 | |

TABLE 2-continued

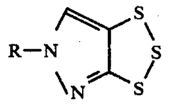

| R | mp° C. |
|---|---|
| 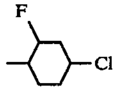 | |

Illustrative compounds which can be prepared using the general procedure of Examples 3 and 5 are shown in Table 3.

TABLE 3

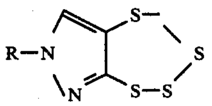

| R | mp° C. |
|---|---|
| H | 129–133 |
| $-CH_3$ | 114–116 |
| $-C_2H_5$ | 54–56 |
| $-CH_2CH_2CH_3$ | |
| $-CH(CH_3)_2$ | |
| $-CH_2CH_2CH_2CH_3$ | |
| $CH_3$<br>\|<br>$-CHCH_2CH_2CH_3$ | |
| $-CH_2CH(CH_3)_2$ | |
| $-C(CH_3)_3$ | |
| 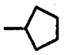 | |
| 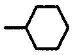 | 73–75 |
| 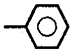 | 113–115 |
| 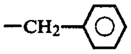 | |
| 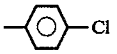 | |
| 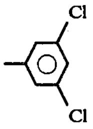 | |
| 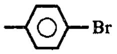 | |
| 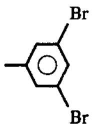 | |
| 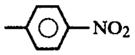 | |
| 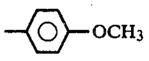 | |
| 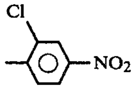 | |
| 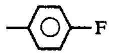 | |

TABLE 3-continued

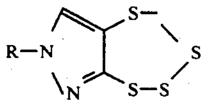

| R | mp° C. |
|---|---|
| 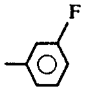 | |
| 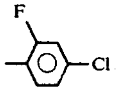 | |

Formulations

Useful formulations of the compounds of Formula I can be prepared in conventional ways. They include dusts, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 1.0% to 99% by weight of active ingredient(s) and at least one of (a) about 0.1% to 20% surfactant(s) and (b) about 1% to 99.0% solid or liquid diluent(s). More specifically, they will contain these ingredients in the approximate proportions set forth in Table 1.

TABLE 1

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Solutions | 5–50 | 40–95 | 0–15 |
| Emulsions (including Emulsifiable Concentrates Aqueous Suspensions | 10–50 | 40–84 | 1–20 |
| Dusts | 1–25 | 70–99 | 0–5 |
| High Strength Compositions | 90–99 | 0–10 | 0–2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

Agricultural compositions, i.e., formulations which contain the compounds of this invention as active ingredient, may also contain other active ingredients such as conventional insecticides, miticides, bactericides, nematicides, fungicides, or other agricultural chemicals, such as fruit set agents, fruit thinning compounds, fertilizer ingredients, and the like. The additional agricultural chemicals are employed in mixtures or combinations in amounts ranging from one-tenth to twenty times that of the compound or compounds of this invention. The proper choice of amounts is readily made by one skilled in the art of protecting plants from pest depredations. The following are illustrative of the agricultural chemicals that may be included in compositions or added to sprays containing one or more of the active compounds of this invention:

bis(dimethylthiocarbamoyl)disulfide; or
tetramethylthiuram disulfide (thiram);
metal salts of ethylenebisdithiocarbamic acid or propylenebisdithiocarbamic acids, e.g., manganese, zinc, iron and sodium salts (maneb or zineb);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2-tetrachloroethyl)thio]-4-cyclohexene-1,2-dicarboximide (captafol);
2,4-dichloro-6-(o-chloroanilino)-s-triazine (anilazine);
3,3'-ethylenebis(tetrahydro-4,6-dimethyl-2H-1,3,5-thiadiazine-2-thione), (milneb);
triphenyltin hydroxide (fentin hydroxide);
triphenyltin acetate (fentin acetate);
N'-dichlorofluoromethylthio-N,N-dimethyl-N'-phenylsulfamide (dichlorofluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate (carbendazim);
1,2-bis(3-methoxycarbonyl-2-thioureido)benzene (methyl thiophanate);
2-cyano-N-(ethylcarbamoyl)-2-methoxyiminoacetamide (cymoxamide)

The agricultural chemicals listed above are merely exemplary of compounds that mey be mixed with the active compounds of this invention to broaden the spectrum of disease control.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Little, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, N.Y., 1963, pp. 8-59ff.

For further information regarding the art of formulation, see for example:

J. B. Buchanan, U.S. Pat. No. 3,576,834, Apr. 27, 1971, Col. 5, Line 36 through Col. 7, Line 70 and Ex. 1–4, 17, 106, 123–140;

R. R. Shaffer, U.S. Pat. No. 3,560,616, Feb. 2, 1971, Col. 3, Line 48 through Col. 7, Line 26 and Examples 3-9, 11-18.

E. Somers, "Formulation", Chapter 6 in Torgeson, "Fungicides", Vol. I, Academic Press, N.Y., 1967.

Example A

| Dust | |
|---|---|
| 7-methyl-7H-1,2,3,4,5-petathiepino[6,7-c]pyrazole | 10% |
| Attapulgite | 10% |
| Talc | 80% |

The active ingredient is blended with attapulgite and then passed through a hammer mill to produce particles substantially all below 200 microns. The ground concentrate is then blended with powdered talc until homogeneous. All compounds of the invention may be formulated in like manner.

Example B

| Aqueous Suspension | |
|---|---|
| 7-methyl-7H-1,2,3,4,5-pentathiepino[6,7-c]pyrazole | 50.0% |
| Polyacrylic acid thickener | 0.3% |
| Dodecylphenol polyethylene glycol ether | 0.5% |
| Disodium phosphate | 1.0% |
| Monosodium phosphate | 0.5% |
| Polyvinyl alcohol | 1.0% |
| Pentachlorophenol | 0.4% |
| Water | 46.3% |

The ingredients are ground together in a sand mill to produce particles essentially all under five microns in size.

Example C

| High Strength Concentrate | |
|---|---|
| 7-methyl-7H-1,2,3,4,5-pentathiepino[6,7-c]pyrazole | 99% |
| Trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

Example D

| Wettable Powder | |
|---|---|
| 7-methyl-7H-1,2,3,4,5-pentathiepino[6,7-c]pyrazole | 80% |
| Sodium alkylnaphthalenesulfonate | 2% |
| Sodium ligninsulfonate | 2% |
| Synthetic amorphous silica | 3% |
| Kaolinite | 13% |

The above ingredients are blended into a uniform mixture which is hammer-milled and then air-milled into a wettable powder. The particle size of the wettable powder, as determined by Coulter Counter, is less than 5 microns, average.

Example E

| Oil Suspension | |
|---|---|
| 7-methyl-7H-1,2,3,4,5-pentathiepino[6,7-c]pyrazole | 25% |
| Polyoxyethylene sorbitol hexaoleate | 5% |
| Highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Example F

| Wettable Powder | |
|---|---|
| 7-methyl-7H-1,2,3,4,5-pentathiepino[6,7-c]pyrazole | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active essentially all below 10 microns in diameter. The product is reblended before packaging.

Example G

| Solution | |
|---|---|
| 7-methyl-7H-1,2,3,4,5-pentathiepino[6,7-c]pyrazole | 5% |
| Dimethylformamide | 95% |

The ingredients are combined and stirred to produce a solution, which can be used for low volume applications.

Example H

| Wettable Powder | |
|---|---|
| 2-methyl-2H-1,3-dithiolo[4,5-c]-pyrazole-5-thione | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active essentially all below 10 microns in diameter. The product is reblended before packaging.

Example I

| Wettable Powder | |
|---|---|
| 7-phenyl-7H-1,2,3,4,5-pentathiepino[6,7-c]-pyrazole | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active essentially all below 10 microns in diameter. The product is reblended before packaging.

Example J

| | |
|---|---|
| 7-Cyclohexyl-7H-1,2,3,4,5-penta-thiepino[6,7-c]-pyrazole | 10% |
| Dimethylformamide | 90% |

The ingredients are combined and stirred to produce a solution which can be used for low volume applications.

Example K

| Wettable Powder | |
|---|---|
| 7-H-1,2,3,4,5-penta-thiepino[6,7-c]pyrazole | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active essentially all below 10 microns in diameter. The product is reblended before packaging.

Biological Utility

The compounds of this invention are effective for control of a broad spectrum of plant diseases on a variety of host plants with a margin of plant safety. The diseases are incited by fungal pathogens represented by, but not limited to, *Venturia inaequalis, Phytophthora infestans, Erysiphe cichoracearum, Puccinia graminis* var. tritici, *Uromyces phaseoli,* and *Cercospora beticola.*

Disease control is accomplished by applying the compounds of this invention to the portion of the plant to be protected. The compounds may be applied as preventive treatments prior to inoculation with the pathogen, or after inoculation as a curative post-infection treatment.

Rates of application for compounds of this invention will be influenced by specific host plants, fungal pathogens, and many factors of the environment must be determined under use conditions. Foliage sprayed with concentrations ranging from 1 to 500 ppm active ingredient can be protected from disease under suitable conditions.

In the following examples, which more clearly illustrate the biological activity of the compounds of this invention, percent disease control was calculated by the formula $$100 - \left[ \frac{\text{disease rating on treated plants}}{\text{disease rating on untreated plants}} \times 100 \right] = \text{percent control}$$

No plant injury was noted when host plants specified in the following examples were treated with compounds of this invention at the specified application rates.

Example I

7-Methyl-7H-1,2,3,4,5-pentathiepino[6,7-c]-pyrazole was dissolved in acetone in an amount equal to 10% of the final volume and then suspended at a concentration of 80 ppm in purified water containing 250 ppm of the surfactant Trem® 014 (polyhydric alcohol esters). This suspension was sprayed to the point of run-off on 6-week-old tomato plants. The following day, the plants were inoculated with a spore suspension of *Phytophthora infestans* and incubated in a saturated humidity chamber at 20° for 24 hours and then in a greenhouse for an additional 4 days when disease ratings were made. The compound 7-methyl-7H,1,2,3,4,5-pentathiepino[6,7-c]pyrazole, provided excellent disease control as treated plants had only a few foliar lesions (99% control) in contrast to untreated plants which were covered with late blight lesions.

Example II

7-Methyl-7H-1,2,3,4,5-pentathiepino[6,7-c]-pyrazole was dissolved in acetone in an amount equal to 10% of the final volume and then suspended at a concentration of 80 ppm in purified water containing the surfactant Trem® 014 (polyhydric alcohol esters). This suspension was sprayed to the point of run-off on Pinto bean seedlings. The following day, the plants were inoculated with a spore suspension of the fungus *Uromyces phaseoli* var. typica and incubated in a saturated humidity chamber at 20° C. for 24 hours, and then in a greenhouse for an additional 7 days when disease ratings were made. The compound, 7-methyl-7H-1,2,3,4,5-pentathiepino[6,7-c]pyrazole, provides complete disease control, as treated plants were free of foliar lesions in contrast to untreated plants, which were covered with rust pustules.

Example III

Compounds of this invention were dissolved in acetone in an amount equal to 10% of the final volume and then suspended at a concentration of 80 ppm in purified water containing 250 ppm of the surfactant Trem® 014 (polyhydric alcohol esters). This suspension was sprayed to the point of run-off on seedling apple plants. The following day, the plants were inoculated with a spore suspension of the fungus *Venturia inaequalis* and incubated in a saturated humidity chamber at 20° for 24 hours, and then in a greenhouse for an additional 11 days when disease ratings were made. As shown in Table IV, compounds of this invention provided excellent disease control, as treated plants had only a few foliar lesions in contrast to untreated plants, which were covered with scab lesions.

Example IV

Compounds of this invention were dissolved in acetone in an amount equal to 10% of the final volume and then suspended at a concentration of 80 ppm in purified water containing 250 ppm of the surfactant Trem® 014 (polyhydric alcohol esters). This suspension was sprayed to the point of run-off on 2-week-old cucumber plants. The following day, the plants were inoculated with a spore suspension of the fungus [Erysiphe cichoracearum and incubated in a greenhouse for 8 days when disease ratings were made. As shown in Table IV, compounds of this invention provided excellent disease control, as treated plants had no or very few foliar lesions in contrast to untreated plants which were covered with powdery mildew.

Example V

Compounds of this invention were dissolved in acetone in an amount equal to 10% of the final volume and then suspended at a concentration of 80 ppm in purified water containing 250 ppm of the surfactant Trem® 014 (polyhydric alcohol esters). This suspension was sprayed to the point of run-off on wheat seedlings. The following day, the plants were inoculated with a spore suspension of *Puccinia graminis* var. tritici and incubated in a saturated humidity chamber at 20° C. for 24 hours and then in a greenhouse for an additional 7 days when disease ratings were made. As shown in in Table IV, the compounds of this invention provided excellent disease control, as treated plants had no or only a few rust pustules in contrast to untreated plants which had numerous rust pustules on each leaf.

Example VI

Compounds of this invention were dissolved in acetone in an amount equal to 10% of the final volume and then suspended at a concentration of 80 ppm in purified water containing 500 ppm of the surfactant Trem ® 014 (polyhydric alcohol esters). This suspension was sprayed to the point of run-off on 6–8 week-old sugar beet seedlings. The following day, the seedlings were inoculated with a spore suspension of the fungus *Cercospora beticola* and incubated in a saturated humidity chamber at 22°–26° C. for 72 hours. After 21 days additional incubation in a greenhouse, disease ratings were made. As shown in Table IV, compounds of this invention provided excellent disease control as treated plants had only a few foliar lesions in contrast to untreated plants, which had numerous leaf spot lesions on each leaf.

TABLE IV

| | Preventive % Disease Control | | | | | |
|---|---|---|---|---|---|---|
| Compound | Apple Scab | Tomato Late Blight | Cucumber Powdery Mildew | Wheat Rust | Bean Rust | Sugar Beet Cercospora |
| 7-methyl-7H-1,2,3,4,5-pentathiepino[6,7-c]-pyrazole | 100 | 99 | 99 | 100 | 100 | 85 |
| 7-phenyl-7H-1,2,3,4,5-pentathiepino[6,7-c]-pyraole | 94 | 20 | 100 | 98 | 86 | 19 |
| 2-methyl-2H-1,3-dithiolo-[4,5-C]pyrazole-5-thione | 82 | 22 | 100 | 100 | 99 | 76 |
| 7-cyclohexyl-7H-1,2,3,4,5-pentathiepino-[6,7-c]pyrazole | 100 | 0* | 98 | 0* | not tested | not tested |
| 2-cyclohexyl-2H-1,3-dithiol-[4,5-c]pyrazole-5-thione | 92 0* | 100* | 95 | not | not tested | tested |
| 7H-1,2,3,4,5-pentathiepino-[6,7-c]pyrazole | 93* | 83* | 65* | 90* | not tested | not tested |

*at 100 ppm

Example VII

The curative effect of 7-methyl-7H-1,2,3,4,5-pentathiepino[6,7-c]pyrazole was demonstrated on seedling apple plants. Plants were inoculated with a spore suspension of the fungus *Venturia inaequalis* and incubated in a saturated humidity chamber at 20° C. for 24 hours, then placed in a greenhouse for an additional 24 hours. Forty-eight hours after inoculation, plants were sprayed to the point of run-off with a suspension containing the compounds of this invention. This suspension was prepared by dissolving the compound in acetone in an amount equal to 10% of this final volume and then suspending at a concentration of 80 ppm in purified water containing 250 ppm of the surfactant Trem ® 014 (polyhydric alcohol esters). Plants were then incubated in a saturated humidity chamber at 20° C. for 12 hours and then in a greenhouse for an additional 11 days, when disease ratings were made. The compound, 7-methyl-7H-1,2,3,4,5-pentathiepino[6,7-c]-pyrazole, provided excellent disease control (79% control), as treated plants had only a few foliar lesions in contrast to untreated plants which were covered by scab lesions.

Example VIII

The curative effects of 7-methyl-7H-1,2,3,4,5-pentathiepino[6,7-c]pyrazole was demonstrated on 6–8 week-old sugar beet plants. Plants were inoculated with a spore suspension of the fungus *Cercospora beticola* and incubated alternately in a saturated humidity chamber at 22°–26° C. for 17 hours, then in a greenhouse for 7 hours. Forty-eight hours following inoculation, plants were sprayed to the point of run-off with a suspension containing the compounds of this invention. This suspension was prepared by dissolving the compound in acetone in an amount equal to 10% of the final volume and then suspending at a concentration of 80 ppm in purified water containing 500 ppm of the surfactant Trem ® 014 (polyhydric alcohol esters). Plants were then returned to the alternately wet/dry incubation schudule for a total duration of 96 hours. After 21 days additional incubation in a greenhouse, disease ratings were made. Plants treated with 7-methyl-7H-1,2,3,4,5-pentathiepino[6,7-c]pyrazole had only a few foliar lesions (90% control) in contrast to untreated plants which had numerous leaf spot lesions on each leaf.

What is claimed is:

1. A compound of the formula

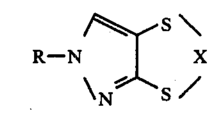

wherein

X is —S—S—S— or

;

and

R is H, $C_1$–$C_6$ alkyl, $C_5$–$C_6$ cycloalkyl,

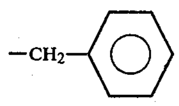

or 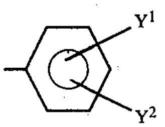

$Y^1$ and $Y^2$ independently are H, F, Cl, Br, p-methoxy or p-nitro.

2. A compound of claim 1 where X is —S—S—S—.

3. A compound of claim 1 where X is >C═S and R is H, $C_1$–$C_6$ alkyl, $C_5$–$C_6$ cycloalkyl or phenyl.

4. A compound of claim 1 where X is —S—S—S— and R is H, $C_1$–$C_6$ alkyl, $C_5$–$C_6$ cycloalkyl or phenyl.

5. The compound of claim 1 which is 7-methyl-7H-1,2,3,4,5-pentathiepino[6,7-c]pyrazole.

6. The compound of claim 1 which is 7-phenyl-7H-1,2,3,4,5-pentathiepino[6,7-c]pyrazole.

7. The compound of claim 1 which is 7-cyclohexyl-7H-1,2,3,4,5-pentathiepino[6,7-c]pyrazole.

8. The compound of claim 1 which is 7H-1,2,3,4,5-pentathiepino[6,7-c]pyrazole.

9. The compound of claim 1 which is 2-methyl-2H-1,3-dithiolo[4,5-c]pyrazole-5-thione.

10. The compound of claim 1 which is 2-cyclohexyl-2H-1,3-dithiolo[4,5-c]pyrazole-5-thione.

11. An agricultural fungicidal composition consisting essentially of a surfactant, diluent or mixtures thereof and an effective fungicidal amount of a compound of claim 1.

12. An agricultural fungicidal composition consisting essentially of a surfactant, diluent or mixtures thereof and an effective fungicidal amount of a compound of claim 2.

13. An agricultural fungicidal composition consisting essentially of a surfactant, diluent or mixtures thereof and an effective fungicidal amount of a compound of claim 3.

14. An agricultural fungicidal composition consisting essentially of a surfactant, diluent or mixtures thereof and an effective fungicidal amount of a compound of claim 4.

15. An agricultural fungicidal composition consisting essentially of a surfactant, diluent or mixtures thereof and an effective fungicidal amount of the compound of claim 5.

16. An agricultural fungicidal composition consisting essentially of a surfactant, diluent or mixtures thereof and an effective fungicidal amount of the compound of claim 6.

17. An agricultural fungicidal composition consisting essentially of a surfactant, diluent or mixtures thereof and an effective fungicidal amount of the compound of claim 7.

18. An agircultural fungicidal composition consisting essentially of a surfactant, diluent or mixtures thereof and an effective fungicidal amount of the compound of claim 8.

19. An agircultural fungicidal composition consisting essentially of a surfactant, diluent or mixtures thereof and an effective fungicidal amount of the compound of claim 9.

20. An agricultural fungicidal composition consisting essentially of a surfactant, diluent or mixtures thereof and an effective fungicidal amount of the compound of claim 10.

21. A method for control of fungi on plants which comprises applying to a plant to be protected a fungicidally effective amount of a compound of claim 1.

22. A method for control of fungi on plants which comprises applying to a plant to be protected a fungicidally effective amount of a compound of claim 2.

23. A method for control of fungi on plants which comprises applying to a plant to be protected a fungicidally effective amount of a compound of claim 3.

24. A method for control of fungi on plants which comprises applying to a plant to be protected a fungicidally effective amount of a compound of claim 4.

25. A method for control of fungi on plants which comprises applying to a plant to be protected a fungicidally effective amount of the compound of claim 5.

26. A method for control of fungi on plants which comprises applying to a plant to be protected a fungicidally effective amount of the compound of claim 6.

27. A method for control of fungi on plants which comprises applying to a plant to be protected a fungicidal effective amount of the compound of claim 7.

28. A method for control of fungi on plants which comprises applying to a plant to be protected a fungicidal effective amount of the compound of claim 8.

29. A method for control of fungi on plants which comprises applying to a plant to be protected a fungicidal effective amount of the compound of claim 9.

30. A method for control of fungi on plants which comprises applying to a plant to be protected a fungicidal effective amount of the compound of claim 10.

* * * * *